(12) United States Patent
Pratt et al.

(10) Patent No.: US 10,993,752 B2
(45) Date of Patent: May 4, 2021

(54) STERNOTOMY CLOSURE TECHNIQUE USING POLYMERIC CABLE

(71) Applicant: KINAMED, INC., Camarillo, CA (US)

(72) Inventors: Clyde Ronald Pratt, Somis, CA (US); Adam Lee Nelson, Camarillo, CA (US); Robert Arthur Bruce, Ventura, CA (US); Vineet Kumar Sarin, Moorpark, CA (US)

(73) Assignee: KINAMED, INC., Camarillo, CA (US)

( * ) Notice: Subject to any disclaimer, the term of this patent is extended or adjusted under 35 U.S.C. 154(b) by 0 days.

(21) Appl. No.: 15/875,221

(22) Filed: Jan. 19, 2018

(65) Prior Publication Data

US 2018/0199968 A1 Jul. 19, 2018

Related U.S. Application Data

(60) Provisional application No. 62/448,309, filed on Jan. 19, 2017.

(51) Int. Cl.
*A61B 17/82* (2006.01)
*A61B 17/17* (2006.01)
(Continued)

(52) U.S. Cl.
CPC ........ *A61B 17/823* (2013.01); *A61B 17/1789* (2016.11); *A61B 17/842* (2013.01);
(Continued)

(58) Field of Classification Search
CPC . A61B 17/823; A61B 17/1789; A61B 17/842; A61B 17/8869; A61B 17/8861; A61B 2090/065; A61B 17/82
(Continued)

(56) References Cited

U.S. PATENT DOCUMENTS 5,852,926 A * 12/1998 Breedlove ................ D02G 3/36
57/210
6,589,246 B1 7/2003 Hack et al.
(Continued)

FOREIGN PATENT DOCUMENTS

JP 2008-167869 7/2008
WO WO2006/060911 A1 6/2006

OTHER PUBLICATIONS

Adams, J. et al. Comparison of Force Exerted on the Sternum During a Sneeze Versus During Low-, Moderate-, and High-Intensity Bench Press Resistance Exercise With and Without the Valsalva Maneuver in Healthy Volunteers, Elsevier Inc. (2014).
(Continued)

*Primary Examiner* — Ellen C Hammond
*Assistant Examiner* — David C Comstock
(74) *Attorney, Agent, or Firm* — Warner Norcross + Judd LLP (57) ABSTRACT

A sternotomy closure technique is suitably carried out with a cerclage mechanism which is capable of maintaining proper bony compression (within a desired range) across the sternum cut, in spite of a range of external forces and significant lateral distraction due to these external forces. The sternum fragments are aligned in apposition disposed around a longitudinal seam and secured with a resilient element. The resilient element is tensioned to a desired tension to compress the sternum to a desired compression range. The resilient element is then elongated and contracted while accepting multiple cycles of physiological distracting forces across the sternum while maintaining contact pressure across the longitudinal seam within a desired range for a length of time sufficient for bony healing. The resilient element is preferably a polymer cable comprising an elongated elastic polymeric core coaxially surrounded by a
(Continued)

sheath woven from ultra-high molecular weight polyethylene strands.

18 Claims, 3 Drawing Sheets

(51) Int. Cl.
    *A61B 17/84*     (2006.01)
    *A61B 17/88*     (2006.01)
    *A61B 90/00*     (2016.01)

(52) U.S. Cl.
    CPC ...... *A61B 17/8869* (2013.01); *A61B 17/8861* (2013.01); *A61B 2090/065* (2016.02)

(58) Field of Classification Search
    USPC .............................. 606/60, 74, 102, 103, 105
    See application file for complete search history.

(56) References Cited

U.S. PATENT DOCUMENTS

| | | | |
|---|---|---|---|
| 7,207,090 B2 | 4/2007 | Mattchen | |
| 8,469,967 B2 | 6/2013 | Pratt et al. | |
| 9,107,720 B2 | 8/2015 | Pratt et al. | |
| 9,642,661 B2* | 5/2017 | Stone | A61B 17/0401 |
| 2006/0052782 A1* | 3/2006 | Morgan | A61B 90/06 606/60 |
| 2007/0233065 A1* | 10/2007 | Donofrio | A61B 8/4472 606/309 |
| 2010/0087872 A1 | 4/2010 | Morihara et al. | |
| 2010/0094294 A1* | 4/2010 | Gillard | A61B 17/823 606/74 |
| 2010/0106194 A1* | 4/2010 | Bonutti | A61B 17/0218 606/279 |
| 2012/0109129 A1* | 5/2012 | Bernstein | A61B 17/823 606/74 |
| 2012/0130180 A1* | 5/2012 | Pell | A61B 5/0051 600/206 |
| 2012/0330351 A1* | 12/2012 | Friedman | A61B 17/12013 606/205 |
| 2014/0142638 A1 | 5/2014 | Goodwin | |
| 2015/0127004 A1* | 5/2015 | Patil | A61B 17/823 606/74 |
| 2015/0297274 A1* | 10/2015 | Dreyfuss | A61B 17/82 606/74 |
| 2019/0099207 A1* | 4/2019 | Houff | A61B 17/823 |

OTHER PUBLICATIONS

Cohen D. et al., A Biomechanical Comparison of Three Sternotomy Closure Techniques, Elsevier Science, p. 563-568 (2002).
Glennie, S. et al., Strength of wired sternotomy closures: effect of number of wire twists, Interactive Cadiovascular and Thoracic Surgery, p. 3-5 (2003).
Khasati, N. et al., Is the figure-of-eight superior to the simple wire technique for closure of the sternum?, Interactive Cardiovascular and Thoracic Surgery, p. 191-194 (2003).
Kilian, E. et al., Sternal closure after median sternotomy: a new technique using titanium hooks and wires applied parasternally, Interactive Cardio Vascular and Thoracic Surgery, p. 721-724 (2013).
Thrumble, D. et al., Validation of a Bone Analog Model for Studies of Sternal Closure, Elsevier Science, p. 739-744 (2002).
International Search Report and Written Opinion, International Application No. PCT/US2018/014498, dated Jul. 9, 2018.
Office Action Japan Patent Application No. 2019-539278 dated Nov. 4, 2020.
SuperCable Surgical Technique <URL: https://www.surgicalspecialties.com.au/system/resources/W1siZiIsIjIwMTYvMDUvMjMvMDRfN TdfMzZfMzE2X1NUX0IwMDExMEdfU3VwZXJDYWJsZV9Td XJnaWNhbF9UZNobmlxdWUucGRmIl1d/ST_B00110G%20SuperCable%20Surgical%20Technique.pdf>.

\* cited by examiner

Ref: Pioneer Surgical Technology Brochure

STERNOTOMY CLOSURE TECHNIQUE USING POLYMERIC CABLE

RELATED APPLICATIONS

This application claims the benefit of provisional patent application No. 62/448,309 to C. Pratt et al., filed Jan. 19, 2017.

BACKGROUND

Many surgeries involving the heart and other thoracic structures require full access to areas inside the chest. Generally, this access is obtained by splitting the sternum by a full length osteotomy: using a saw to divide the sternum from its superior pole to its inferior pole. This osteotomy of the sternum is commonly referred to as a median sternotomy. In the US, approximately 700,000 sternal osteotomies (i.e. sternotomies) are performed every year.

Upon completion of open heart surgery (or other surgery requiring access to the chest cavity, such as a lung transplant for example), the sternum must be closed. Usually this involves binding the two divided halves of the sternum together using a cerclage technique. The objective is to bring the two bone segments into proper apposition so that they may heal and again provide the normal function of the sternum in the musculo-skeletal system. The desired outcome is full bony union so that the sternum is restored as nearly as possible to its pre-surgical condition. In order to achieve this goal, the closure must be sufficiently robust so that full bone formation and healing can occur across the sternotomy.

Most sternotomy closures are performed using stainless steel or other metallic alloy wire, with the aid of instruments such as a wire tightener and wire cutters. Braided metallic cable may be used, either alone or in conjunction with bone fixation devices such as plates, screws, or the like.

Conventional methods often fail to achieve high-quality bony union. Reliable bone healing requires good bone fragment stability and close approximation of fragments with minimum gap extension. Poor stability and excessive gap extension can lead to non-union, fibro-osseous-union, or partial bony union. Poor stability and bone healing after median sternotomy contribute to a number of potential complications ranging from long-term patient discomfort to acute dehiscence and deep sternal wound infection (mediastinitis), with very high treatment costs, and high patient morbidity and mortality rates.

A number of factors negatively influence the success of sternal closure. These factors include the failure to accurately quantify and apply a controlled tightening force (load) across the divided bone, failure to maintain bony apposition in the correct position, allowance of too much motion (or too little), and failure to transmit load across the osteotomy during the healing period. Further factors include a tendency of wire or metallic cable to cut through bone and soft tissue due to movement and/or force, loss of fixation due to fatigue of the metallic wire or cable, or breakage of the metallic wire or cable itself due to fatigue. Furthermore, wound healing or the systemic health of the patient may be impacted by metal ions released from metal wires, cables, plates and screws.

For best healing, three factors must be present: bony apposition, restricted movement, and force transmission across the osteotomy plane. In all cases, adequate blood supply must be present for healing.

In order to stabilize the reassembled (divided) sternum, forces must be applied to the bone sections so that they are held together during the normal activities that occur during the healing process. This is particularly challenging as the sternum experiences variable and often transient forces transmitted through the ribs or other tissues, during activities such as breathing, coughing, moving, lying down, rising, and other activities of daily living. For example, sneezing has been shown to generate as much as 814 Newtons of lateral distraction force on the sternum.

SUMMARY

A sternotomy closure technique using polymeric cable is presented which accomplishes many of the goals noted above. The technique is suitably carried out with a cerclage mechanism as described herein, which is capable of maintaining proper bony compression (within a desired range) across the sternotomy cut, in spite of a range of external forces and significant lateral distraction due to these external forces.

The present method secures a divided sternum during a healing period. The sternum fragments are aligned in apposition disposed around a longitudinal seam and secured with a resilient element. The resilient element is tensioned to a desired tension to compress the sternum halves to a desired compression range. The resilient element is then elongated and contracted while accepting multiple cycles of physiological distracting forces across the sternum while maintaining contact pressure across the longitudinal seam within a desired range for a length of time sufficient for bony healing. The resilient element is preferably a polymer cable comprising an elongated elastic polymeric core coaxially surrounded by a sheath woven from ultra-high molecular-weight polyethylene strands.

These and other features, aspects, and advantages of the present invention will become better understood with reference to the following drawings, description, and claims.

DETAILED DESCRIPTION OF THE INVENTION

Rather than steel or other metallic wire or cable, the present sternotomy closure technique preferably employs a polymeric engineered cable available from Kinamed, Inc. in Camarillo, Calif. and sold under the name "SuperCable." The cable is constructed from an elongated elastic polymeric core, suitably Nylon, coaxially surrounded by a sheath woven from ultra-high molecular-weight polyethylene strands. Further information and description of this "SuperCable" is given in U.S. Pat. No. 6,589,246 to Mattchen (incorporated herein by reference). This cable is very flexible, elastic, with high fatigue strength and tensile strength. Such cable is capable of repeated cycles of extension/contraction during the healing phase while maintaining the ability to provide compressive load across the osteotomy plane.

Figure 1:
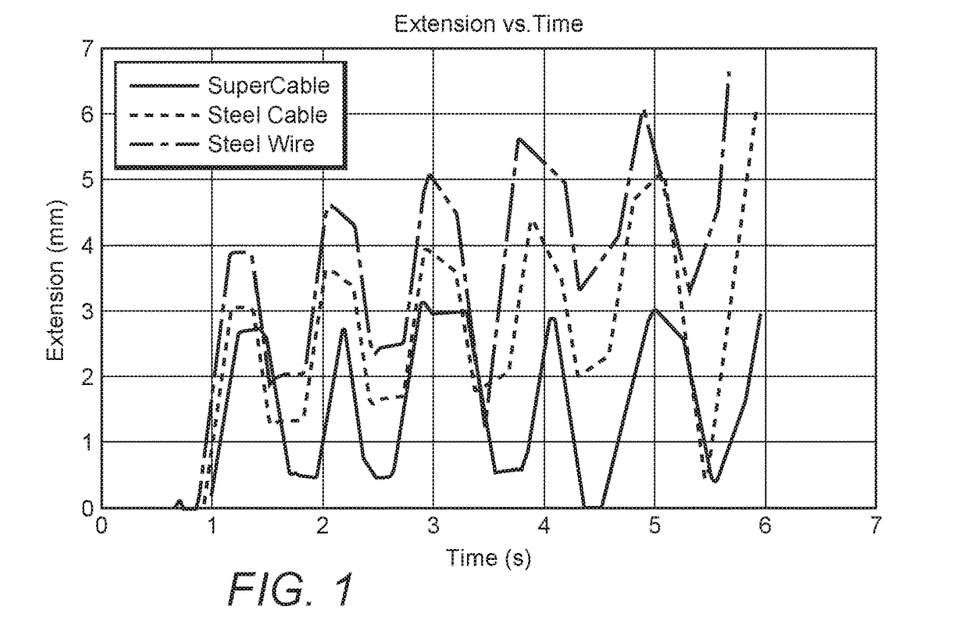
FIG. 1 is a graph illustrating extension versus time for an anatomical sternotomy model that has been secured by 1) a cable in accordance with the invention, 2) steel cable, and 3) steel wire.

FIG. 1 shows cyclical behavior of extension versus time for an anatomical sternotomy model that has been secured by the cable in accordance with the invention. The lower curve represents the "SuperCable" assembly (sternotomy model secured with SuperCables) which consisted for this test of only four SuperCables (each doubled as a circumferential loop). For comparison, similar curves are shown for steel monofilament wire (seven loops, top curve), and for braided steel cable (four loops, middle curve). In each case the sternal halves were forcibly laterally distracted with a cyclic force varying periodically from zero to just over 1000 Newtons, for five cycles using a Chatillon LRX materials testing system. It can be seen that all sternum halves in the test demonstrate extension in response to the application of force. However, the steel cable and steel wire models fail to return to their original position and exhibit greater sternal displacement for a given force after several cycles, as compared to the SuperCable construct. This phenomenon is believed to result from a combination of effects, including irreversible metal cable stretch (or metal wire unwinding) and cut-through into the bone model. Both are believed to contribute to the slackening of the steel wire and steel cable models. In contrast, the SuperCable construct returns repeatedly to its original position even after multiple cycles of stretching and relaxation. In this test, the steel wire (No. 5 steel wire from Ethicon) and steel cable (Pioneer Surgical Technology, now Fusion Innovations) did not maintain the sternum model intact, but the SuperCable model did maintain the model intact after cyclic loading. Both the steel cable- and steel wire-secured sternum completely failed after the loading cycles.

It is believed that the steel wire and cable fail to maintain reliable compressive force across the divided sternum because of at least two factors: first, they have high stiffness and fail to accommodate extensive extension and contraction without losing their initial bone contact length. Much of the elasticity in the full model assembly is believed to lie in the bony model rather than the wire or cable. Metal cables and wires may unwind slightly, thereby lengthening irreversibly. Secondly, such cables tend to bite or cut into the bone, tending to further generate potential for slack in the cerclage. This further tends to generate irreversible slack across the osteotomy plane. Both metal wires and metal cables are known to sometimes cut completely through the sternum, resulting not only in failure to fix the median sternotomy but also bisecting the divided sternum into halves which can significantly complicate a subsequent reconstruction.

Additional testing was performed to support the belief that a more elastic, polymer cable such as "SuperCable" will better maintain pressure between the sternal halves, thereby maintaining stability.

Figure 2:
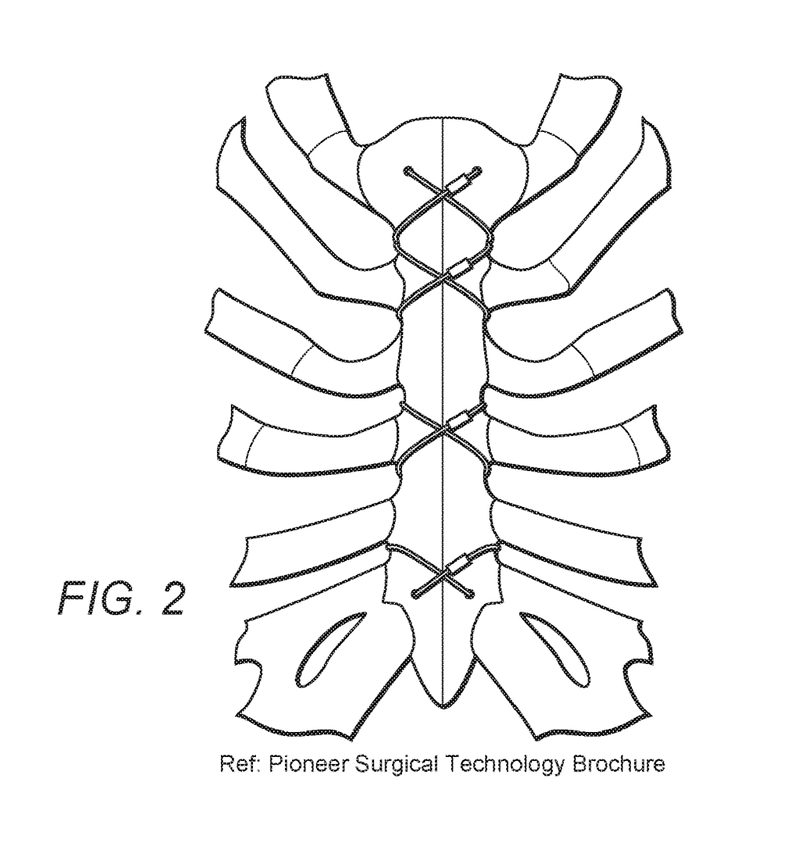
FIG. 2 is a photograph illustrating four stainless steel sternal cables installed on a sternotomy model using a parasternal/transternal "figure-eight" wrapping technique.

Anatomical synthetic sternum models (20 lb/ft$^3$ foam, model number: 1025-2, Sawbones®, Vashon, Wash., USA) were used for testing [Trumble, D. R., McGregor, W. E. & Magovern, J. A. (2002). Validation of a Bone Analog Model for Studies of Sternal Closure. The Annals of Thoracic Surgery, 74(3): 739-745]. The sternum models were potted, divided along their midline, and fixed as follows:

1. Four SuperCables (Kinamed®) in a parasternal wrapping technique at the 1st, 2nd, 4th and 5th intercostal spaces, each tensioned to approximately 80 lbs.
2. Seven No. 5 stainless steel surgical wires (A&E or Ethicon®), 5 of which employed in a parasternal wrapping technique at the 1st through 5th intercostal spaces, 1 placed transternally in the manubrium and 1 placed transternally in the xiphoid. All were tensioned per the manufacturer's instructions and the excess twisted wire was cut off and the cut end turned down towards the surface of the sternum.
3. Four stainless steel sternal cables (Pioneer®) in a parasternal/transternal "figure-eight" wrapping technique as shown in FIG. 2 and tensioned per the manufacturer's recommended procedure.

Prior to testing, all force sensors (SingleTact, model number: CS15-450N, Pressure Profile Systems, Los Angeles, Calif., USA) were calibrated using a standard cyclical run with 10 cycles from ON to ~400 N on a materials testing system (Chatillon, model number: LRX). These calibration values were used to calibrate the raw data obtained by the force sensors during construct testing.

A single, active force sensor was placed consistently within the sternotomy plane on all test samples, adjacent to the 3rd intercostal space with enough offset to avoid interference by the metal wire or cable placements. Four other inactive sensors of the same type were spaced equally along the sternotomy plane to ensure even loading.

Because sneezing can generate 814 Newtons of lateral distraction force on the sternum [Adams, J. et al. (2014). Comparison of Force Exerted on the Sternum During a Sneeze Versus During Low-, Moderate-, and High-Intensity Bench Press Resistance Exercise With and Without the Valsalva Maneuver in Healthy Volunteers. The American Journal of Cardiology, 113(6): 1045-1048], the sternal halves were laterally distracted with a cyclic force ranging from 0 to >800 Newtons for ten cycles using a materials testing system (Chatillon, model number: LRX). The tests were captured on video while measuring and recording forces across the sternal fragments throughout the cyclic loading episode, and after cyclic loading was completed (i.e., with no load being applied).

Figure 3:
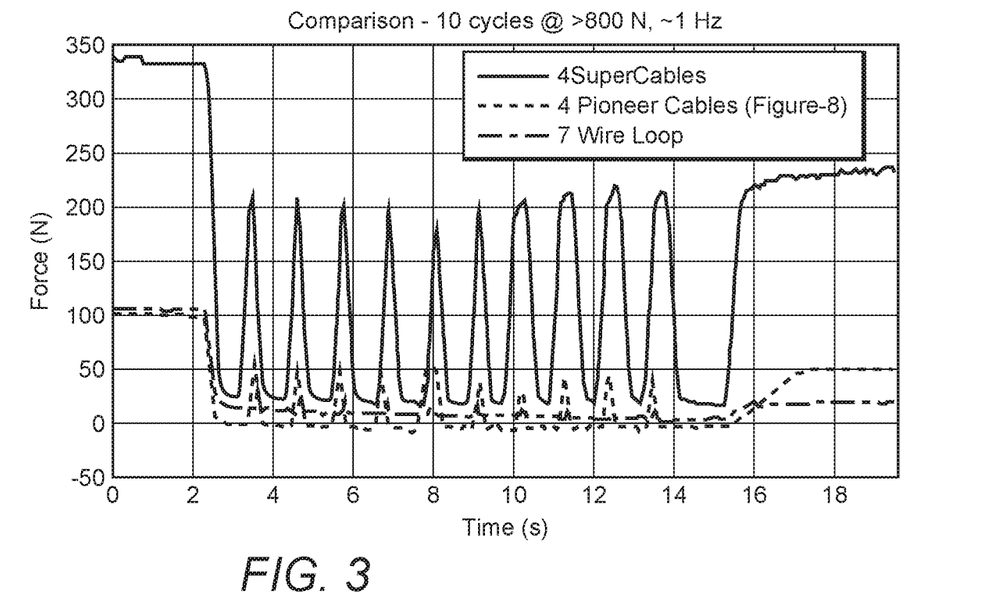
FIG. 3 is a graph showing force as a function of time during the application of a cyclic, time varying lateral distraction force on a sternotomy model for SuperCables, metal cables, and metal wire loops.

FIG. 3 shows the results: the graph shows force (measured by the pressure sensor) as a function of time during the application of cyclic, time varying lateral distraction force. The results are shown for SuperCable, for the metal cables, and for the metal wire loops.

Table 1 summarizes the residual force, percent retention of force, and magnitude of force recovered for all three cable systems.

| Parameter | SuperCable construct | Stainless steel wire construct | Stainless steel cable construct |
|---|---|---|---|
| Residual force between sternal halves after the cyclic loading regime (N) | 237.0 | 18.6 | 49.4 |
| Percent retention of force [residual force after cyclic loading divided by force before cyclic loading] | 71.0% | 17.7% | 49.0% |
| Magnitude of force recovered from the final loading peak to after the entire loading regime (N) | 220.8 | 18.3 | 53.7 |

Figure 4:
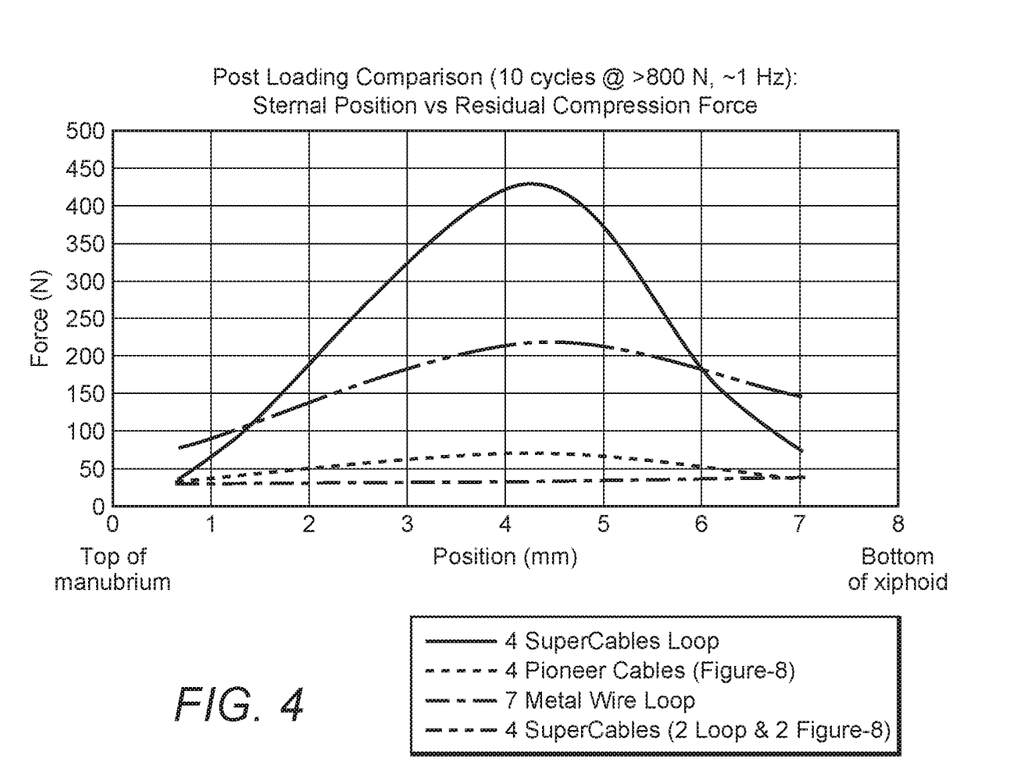
FIG. 4 is a graph showing residual force as a function of location along a sternotomy model for two SuperCable configurations, wire cables, and wire loops.

Additional testing further demonstrates important differences in how the SuperCable construct performed in comparison to the metal wire and metal constructs. The testing outlined above was repeated with two key modifications. First, an additional fixation model was added that included two SuperCables in a parasternal wrapping technique at the $2^{nd}$ & $4^{th}$ intercostal spaces, and two SuperCables in a parasternal/transsternal "figure-eight" wrapping technique at the $1^{st}$ & $5^{th}$ intercostal spaces and transsternally in the manibrium and xiphoid (similar to superior and inferior cables in FIG. 2). Each cable was tensioned to achieve 80 lbs. of compressive force across the divided sternum. Second, two more active force sensors were placed in the sternum models with one each in the manubrium and xiphoid, adjacent to the superior and inferior edges of the models, respectively. All other setup and calibration details were kept consistent. FIG. 4 shows the results: the graph shows residual force (measured by the pressure sensors) as a function of location along the sternotomy models. The results are shown for both SuperCable configurations, for the metal Pioneer cables, and for the metal wire loops. Both of the SuperCable configurations resulted in higher residual force than the metal cables or wire loops in all three sensor locations which is representative of the entire length of the sternotomy models.

A higher residual force between the sternal halves is a measure of the stability after a cyclic loading regime (such as a sneezing or coughing fit) and can be predictive of continued approximation of the sternal halves for the promotion of bony healing. A higher percent retention of force is a measure of whether the residual force after cyclic loading will continue to persist as additional cycles are applied throughout the healing process. A higher magnitude of force recovered is a measure of how much force was absorbed by the sternal closure construct instead of being transmitted to the sternal halves (leading to cut-through into the bone). This absorption of force will logically minimize potential cut-through of the wires/cables since that also minimizes the stress being applied to the sternal halves.

A favorable combination of these parameters should increase the stability of fixation and ensure close approximation of the sternal halves throughout the healing process, resulting in improved healing, reduced patient pain, and reduced potential for complication. This testing has demonstrated that the SuperCable construct delivers superior performance in all three parameters, suggesting that the use of SuperCables should be advantageous in obtaining improved sternal bone healing versus metal wires or cables. It is expected that further study would demonstrate similar results for testing that evaluated the effects of longitudinal shear, transverse shear or a combination of all biomechanical forces to which the sternum is subjected.

In summary, the results of testing demonstrate at least three important differences in how the SuperCable construct performed in comparison to the metal wire and metal cable constructs. These differences are: (1) the residual force between the sternal halves after the cyclic loading, (2) the percent retention of compressive force between sternal halves, and (3) the magnitude of force recovered. The calculated values for these parameters are summarized in Table 1.

Thus, in a first aspect, the invention is a method for securing a divided sternum during a healing period, comprising aligning the sternotomy fragments in apposition disposed around a longitudinal seam; securing the fragments by wrapping with a polymer cable comprising an elongated elastic polymeric core, coaxially surrounded by a sheath woven from ultra-high molecular-weight polyethylene strands; and tensioning the strands to a desired tension to compress the sternum to a desired compression range, such that multiple cycles of physiological distracting forces across the sternum can be accepted while maintaining contact pressure across the longitudinal seam within a desired range to minimize potential cut through, for a length of time sufficient for bony healing. The length of time needed can vary widely depending on variables such as surgical technique and patient compliance, but normally bony healing is reported as requiring 6 to 12 weeks.

The elastic properties of "SuperCable" are believed to be advantageous to absorb shock, equalize load transmitted to the sternum and thus reduce the tendency of cable to cut through the bone.

Figure 5:
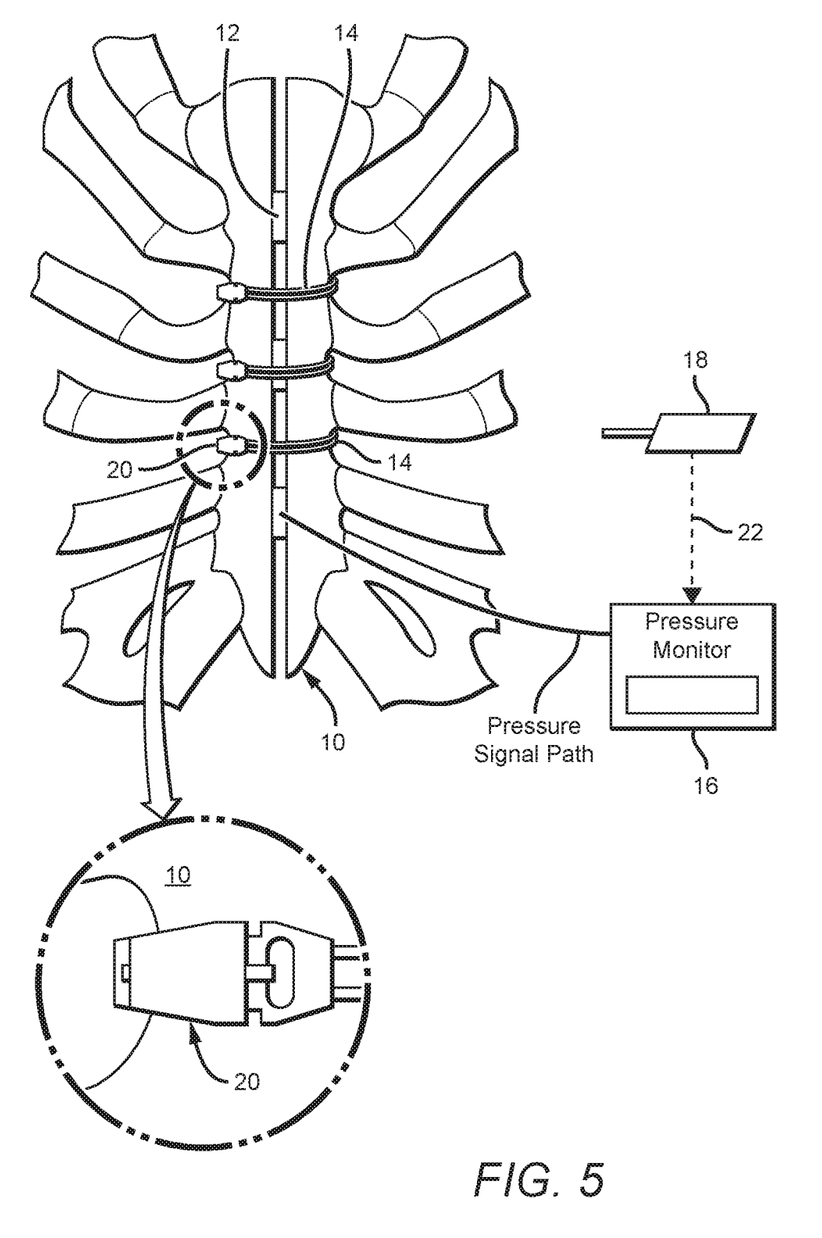
FIG. 5 illustrates one possible embodiment of an apparatus as might be employed when practicing the technique described herein, together with a divided sternum.

One possible embodiment of an apparatus as might be employed when practicing the technique described herein, together with the sternum, is shown in FIG. 5. This arrangement is suitably employed to carry out a "pressure calibration method". Superior results are obtained by a surgical technique to calibrate the relationship between the pressure across the junction (between the sternotomy fragments) and the tension applied to the cerclage cables. In this technique the polymeric "SuperCable" is used, together with a tensioning tool. The tensioning tool is preferably the Super-Cable Cerclage Tensioning Instrument, w/60° Angle, which is commercially available from Kinamed, Inc under catalog number 35-800-7000. The tensioning instrument allows between 80 and 120 lbs (360 to 530 N) of compressive force to be applied across the sternotomy plane by the cables. Improvements and variations of the tensioning tool may be included without departing from the invention.

According to the pressure calibration method, the invention includes a method for securing a divided sternum 10 during a healing period, comprising: aligning the sternum fragments in apposition disposed around a longitudinal seam; inserting at least one thin pressure sensor 12 in the longitudinal seam between the sternum fragments; securing the fragments by wrapping with a polymer cable 14 comprising an elongated elastic polymeric core, coaxially surrounded by a sheath woven from ultra-high molecular-weight polyethylene strands; using a pressure monitor 16 to monitor the pressure sensed by the pressure sensor while applying variable tension on the polymer cable with a tensioning tool 18; detecting a relationship between said variable tension and pressure sensed by the pressure sensor; removing the pressure sensor; tensioning the polymer cable to a desired tension, based upon the detected relationship between variable tension and pressure, to produce a desired pressure in the seam between the sternum fragments; and maintaining said pressure during healing.

According to a more generalized method, the pressure calibration method could be performed using any sufficiently elastic cable or other resilient element, including springs or the like. However, the use of the "SuperCable" (a polymer cable comprising an elongated elastic polymeric core, coaxially surrounded by a sheath woven from ultra-high molecular-weight polyethylene strands) is believed to be very advantageous and to provide an independent source of novelty and advantage.

Pressure sensors are available which are sufficiently thin and accurate to determine the applied pressure. For example, 100 lb (450 N), thin-film, capacitive force sensors are commercially available from Pressure Profiles Systems Inc under catalog number CS15-450N. They are sub-branded as SingleTact sensors and additional information can be found here: https://www.singletact.com/micro-force-sensor/calibrated/sensors/15mm-450-newton/. The sensors are provided calibrated along with open-source software for data capture. Other thin sensors could be used. In a preferred embodiment, multiple sensors are used or a sensor capable of measuring a pressure profile, varying along an axis such as the axis of the sternum cut (seam)—generally from the superior pole (manubrium) to the inferior pole (xiphoid process) of the bone, or along a substantial portion of that axis.

In a preferred embodiment, the pressure calibration method described above is performed together with the first aspect described above.

The pressure calibration method is advantageous because the relationship between tension (in the cerclage) and pressure (across the bony seam) may depend on a number of variables, including the particular anatomical proportions of the patient, the age, sex and weight of the patient, the bony composition and health of the tissues in the sternum, and the particular number and wrapping method chosen by the surgeon. The inventors believe that the pressure across the osteotomy is a more reliable index of optimal fixation as compared to the tension in the cable, which is often the only force metric reported for metal cerclage systems. Based on empirical data, a pressure range (as applied to the cortical bone) of 0.7 to 4.9 Megapascals is believed to be suitable, with the ideal pressure dependent on some or all of the variables listed above.

The pressure calibration method might also be employed as a means to acquire empirical data, which could then be used to provide tensioning guidance during a sternal closure surgery without the need for pressure sensors. For example, empirical testing using pressure sensors could be performed that determines the proper load to be applied for patients of different ages, weights, sexes, bone qualities, etc. In the alternative, pre-operative CT-scan sections, made perpendicular to the osteotomy plane, can be used to quantify the amount of bone present at the level of the sternum wherein the CT "slice" is taken for each patient. As the amount of bone that exists correlates to the load applied to the section by the patient at the slice location, the desired load to be applied in order to assure reliable stability across the osteotomy plane can be deduced. Alternatively, DEXA (dual-energy x-ray absorptiometry) scans could be used as they are routinely utilized to assess bone density and thus bone strength. This data would then be used to determine the proper tension or compressive force to apply (without the need for corresponding pressure sensor information) when performing sternal closure as described herein.

In the invention, the polymer cables can suitably be tensioned and joined by known methods such as a cable lock as described in U.S. Pat. No. 7,207,090. This cable fixation device is currently preferred because it provides secure fixation of polymeric cable at a maintainable, desired tension and because the components are suitably fabricated from materials which minimally interfere with imaging techniques such as magnetic resonance imaging, X-rays and computer aided tomography.

According to yet another aspect of the invention, the polymeric cable cerclage is applied as multiple cables: at least an upper, lower, and central cerclage. Each cable is preferably applied in a loop or "figure-eight" arrangement in either parasternal or transsternal configuration. Each section is then tensioned, potentially in a preferred sequence, preferably to a different tension to achieve or approximate a desired pressure profile across the cut sternum. The different tensions may be achieved in a first variation by simply tensioning the multiple cables differently with a tensioning tool. In another variation, at least one of the three (or more) polymeric cables may be engineered to supply different tension/extension characteristics. For example, at least one of the polymeric cerclage cables fixing the sternum may be engineered to a different strength, stiffness, and/or size than the others by combinations of: varying the core diameter, varying the angles of the weave of the sheath, and/or varying the total size of the cable.

Various numbers of cerclage cables may be used, but a preferred embodiment uses less than six distinct cerclage cables. This is a lower number than typical configurations used with conventional metallic wires; the lower number that is permissible using SuperCable is effective to facilitate convenient and time-efficient closure, without enhancing the risk of cable cutting into the bone; the polymeric cable is believed to have less tendency to abrade and cut into resilient bony surfaces as compared to metal wire or cable.

In addition to its method aspects, the invention includes apparatus aspects. Considered as an apparatus, the invention comprises: a thin pressure transducer 12 capable of insertion between the fragments of a sternum 10 that has been cut into at least two fragments; at least one cerclage cable 14 comprising a polymer cable comprising an elongated elastic polymeric core, coaxially surrounded by a sheath woven from ultra-high molecular weight polyethylene strands, said at least one cable capable of securing said sternum fragments in apposition in proper position to promote bony healing; a pressure monitoring system 16 coupled to said pressure transducer and configured to display pressure sensed by said transducer; a device such as a clasp 20 for securing said cerclage cable in position around the sternum fragments; a tensioning tool 18 capable of applying variable tension to said at least one cerclage cable in response to user manipulation or programming; whereby the user can manipulate said tensioning tool while monitoring the pressure displayed by said pressure monitoring system to determine a relationship between the variable tension and resulting pressure between the sternum fragments, thus determining a desired tension to be applied to said at least one cerclage cable for fixation to obtain a resulting desired pressure.

As with the method aspects, it is preferred that the apparatus include multiple polymer cerclage cables; at least three (upper, lower, central) are preferable. The device for securing the cable may suitably be such as that described in U.S. Pat. No. 7,207,090. Other possible securing devices include, for example, a disposable tensioner, or a plastic clasp such that the entire construct is radiolucent. The fixation tool may suitably be that described in U.S. Pat. No. 9,107,720 or 8,469,967 or available from Kinamed, Inc. as described above, or a variation or improvement of such tool. Further improvements and variants are contemplated within the scope of the invention. For example, in some embodiments the tensioning tool may be coupled mechanically or electrically (22) to the pressure monitoring system to help automate the calibration of pressure in relation to tension. In this context, "calibration" should be understood to mean the action of establishing a relationship between applied cable tension and resulting pressure between the cut surfaces of the osteotomy. For this purpose, a tension sensor (electronic transducer responsive to cable tension or tool torque) can be provided and coupled to the pressure monitoring system or other data processing system. The pressure monitoring system may include tension monitoring and/or data processing capabilities (via either analog processing or digital data processing) to facilitate and display the calibration of pressure to cable tension. The pressure monitoring system may include mechanized or automated tensioning once the desired pressure is programmed by the user. Such variations are also within the scope of the invention and may possess independent sources of novelty.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

We claim:

1. A method for securing a divided sternum during a healing period, comprising the steps:
    aligning sternum fragments in apposition disposed around a longitudinal seam;
    securing the sternum fragments solely with a resilient element having first and second ends and a securing clasp;
    inserting at least one pressure sensor in the longitudinal seam between the sternum fragments;
    tensioning the resilient element to a desired tension to compress the sternum fragments to a desired compression range, said securing clasp arranged to secure said first and second ends of said resilient element and thereby maintain said desired tension on said resilient element; and
    elongating and contracting said resilient element while accepting multiple cycles of physiological distracting forces across the sternum while maintaining contact pressure across the longitudinal seam within a desired range for a length of time sufficient for bony healing.

2. The method of claim 1, wherein said step of securing the sternum fragments solely with a resilient element comprises wrapping the sternum fragments with said resilient element and securing the first and second ends of said resilient element with said securing clasp, and wherein the resilient element is a polymer cable comprising an elongated elastic polymeric core coaxially surrounded by a sheath woven from ultra-high molecular-weight polyethylene strands.

3. A method for securing a divided sternum during a healing period, comprising the steps:
    aligning sternum fragments in apposition disposed around a longitudinal seam;
    securing the sternum fragments solely with a resilient element having first and second ends and a securing clasp;
    inserting at least one pressure sensor in the longitudinal seam between the sternum fragments;
    monitoring a pressure sensed by the pressure sensor while applying variable tension to the resilient element with a tensioning tool;
    detecting a relationship between said variable tension and pressure sensed by the pressure sensor;
    removing the pressure sensor; and
    tensioning the resilient element to a desired tension, based upon the detected relationship between variable tension and pressure, to produce a desired pressure in the longitudinal seam between the sternum fragments, said securing clasp arranged to secure said first and second ends of said resilient element and thereby maintain said desired pressure.

4. The method of claim 3, further comprising securing said resilient element cable around said sternum fragments.

5. The method of claim 3, wherein said at least one pressure sensor comprises at least two pressure sensors, and said at least two pressure sensors are disposed between said sternum fragments in different positions along said longitudinal seam; and wherein said step of pressure monitoring comprises monitoring the at least two pressure sensors independently to determine the pressure sensed by each pressure sensor.

6. The method of claim 3, wherein said desired pressure range is 0.7 to 4.9 Megapascals.

7. The method of claim 3, wherein said step of detecting a relationship between said variable tension and pressure sensed by the pressure sensor comprises processing tension data and pressure data from said pressure sensor with an electronic data processor to determine a relationship function relating applied tension and resulting pressure.

8. The method of claim 3, further comprising automatically controlling with an electronic data processor the step of tensioning said resilient element to a desired tension based upon the detected relationship between variable tension and pressure, to produce a desired pressure in the longitudinal seam between the sternum fragments.

9. The method of claim 3, wherein said resilient element is a polymer cable comprising an elongated elastic polymeric core coaxially surrounded by a sheath woven from ultra-high molecular-weight polyethylene strands.

10. An apparatus for fixing a surgically cut sternum during healing, comprising:
    a pressure transducer inserted between the fragments of a sternum that has been cut into at least two fragments;
    a resilient member wrapped solely around the exterior surfaces of said sternum fragments such that said sternum fragments are secured in apposition in proper position to promote bony healing;
    a pressure monitoring system coupled to the pressure transducer and configured to measure pressure sensed by said transducer; and
    a tensioning tool capable of applying variable tension to said resilient member in response to user manipulation or a programmed digital computer, whereby the user can manipulate said tensioning tool while monitoring the pressure measured by said pressure monitoring system to determine a relationship between the variable tension and resulting pressure between the sternum fragments, thus determining a desired tension to be applied to said resilient member for fixation to obtain a resulting desired pressure.

11. The apparatus of claim 10, wherein the pressure transducer comprises at least two pressure transducers capable of disposition at different points between the fragments of a sternum; the at least two pressure transducers each independently coupled to the pressure monitoring system;
    and wherein said pressure monitoring system is configured to independently monitor each of said at least two pressure transducers.

12. The apparatus of claim 10, further comprising a digital computer programmed to control tensioning automatically in response to the relationship between the variable tension and resulting pressure between the sternum fragments.

13. The apparatus of claim 12, wherein said tensioning is automatically controlled to vary the tension applied to said resilient member.

14. The apparatus of claim 13, wherein said tensioning is automatically controlled to obtain a desired pressure in the range of 0.7 to 4.9 Megapascals.

15. The apparatus of claim 10, wherein said resilient member comprises at least one polymer cable comprising an elongated elastic polymeric core, coaxially surrounded by a sheath woven from ultra-high molecular-weight polyethylene strands, said at least one polymer cable capable of securing said sternum fragments in apposition in proper position to promote bony healing.

16. An apparatus for fixing a divided sternum during healing, comprising:
- a resilient element arranged to secure sternum fragments in apposition in proper position to promote bony healing;
- a pressure transducer arranged for insertion between at least two of said sternum fragments;
- the resilient member capable of sufficient elastic extension to accept multiple cycles of physiological distracting forces across the sternum while maintaining contact pressure across the longitudinal seam within a desired range for a length of time sufficient for bony healing.

17. The apparatus of claim 16, wherein the resilient element is configured to maintain contact pressure in a desired range 0.7 to 4.9 Megapascals during a length of time sufficient for bony healing.

18. The apparatus of claim 16, wherein the resilient element is at least one cerclage cable comprising an elongated elastic polymeric core coaxially surrounded by a sheath woven from ultra-high molecular-weight polyethylene strands, the at least one cable arranged to secure sternum fragments in apposition in proper position to promote bony healing.

* * * * *